United States Patent
Diaz-Chiosa

(10) Patent No.: US 12,138,355 B2
(45) Date of Patent: Nov. 12, 2024

(54) SUTURE WITH TENSION INDICATOR

(71) Applicant: Covidien LP, Mansfield, MA (US)

(72) Inventor: Olesea Diaz-Chiosa, Naugatuck, CT (US)

(73) Assignee: Covidien LP, Mansfield, MA (US)

( * ) Notice: Subject to any disclaimer, the term of this patent is extended or adjusted under 35 U.S.C. 154(b) by 611 days.

(21) Appl. No.: 17/399,323

(22) Filed: Aug. 11, 2021

(65) Prior Publication Data

US 2022/0184270 A1    Jun. 16, 2022

Related U.S. Application Data

(60) Provisional application No. 63/123,598, filed on Dec. 10, 2020.

(51) Int. Cl.
| | |
|---|---|
| *A61B 17/04* | (2006.01) |
| *A61L 17/10* | (2006.01) |
| *A61L 17/14* | (2006.01) |
| *C09C 1/48* | (2006.01) |
| *C09K 11/06* | (2006.01) |
| *A61B 17/06* | (2006.01) |

(52) U.S. Cl.
CPC .......... *A61L 17/145* (2013.01); *A61L 17/105* (2013.01); *C09C 1/48* (2013.01); *C09K 11/06* (2013.01); *A61B 2017/0618* (2013.01); *C09K 2211/10* (2013.01)

(58) Field of Classification Search
CPC .... A61B 17/06166; A61B 2017/06171; A61B 2017/06176; A61B 2017/0618; A61B 2017/06185; A61L 17/00; A61L 17/145
See application file for complete search history.

(56) References Cited

U.S. PATENT DOCUMENTS

| | | | | |
|---|---|---|---|---|
| 5,626,611 | A | | 5/1997 | Liu et al. |
| 6,945,980 | B2 | * | 9/2005 | Nguyen ................. A61B 17/06 606/151 |
| 7,070,610 | B2 | | 7/2006 | Im et al. |
| 9,687,227 | B2 | | 6/2017 | Marczyk et al. |
| 10,728,429 | B2 | | 7/2020 | Derry et al. |
| 11,172,926 | B1 | * | 11/2021 | Moliver ................ A61B 90/92 |
| 2007/0038249 | A1 | * | 2/2007 | Kolster ................. A61B 17/06 606/228 |
| 2008/0078320 | A1 | | 4/2008 | Mattchen et al. |
| 2011/0319932 | A1 | * | 12/2011 | Avelar .................. A61B 90/90 606/228 |
| 2012/0136388 | A1 | | 5/2012 | Odermatt et al. |

(Continued)

OTHER PUBLICATIONS

Extended European Search Report issued in corresponding application EP 21213449.8 dated May 4, 2022 (7 pages).

*Primary Examiner* — Erich G Herbermann
(74) *Attorney, Agent, or Firm* — Weber Rosselli & Cannon LLP

(57) ABSTRACT

A surgical suture provides a visual indication when the suture is subjected to excessive tension. The suture has an inner core at least partially covered by a segmented outer layer. The inner core is not visible when the suture is subjected to acceptable amounts of tension, but will become visible if the suture is subjected to unacceptable amounts of tension. The visibility of the inner core thus indicates to the surgeon or similar medical professional whether or not the suture is under acceptable tension.

20 Claims, 4 Drawing Sheets

(56) References Cited

U.S. PATENT DOCUMENTS

| | | | |
|---|---|---|---|
| 2012/0245602 A1* | 9/2012 | Glick | B29C 65/5071 |
| | | | 606/228 |
| 2015/0073473 A1* | 3/2015 | Broom | A61B 17/06166 |
| | | | 606/228 |
| 2016/0069761 A1* | 3/2016 | Martellaro | G01L 5/101 |
| | | | 702/138 |
| 2020/0129172 A1 | 4/2020 | Dumanian et al. | |

* cited by examiner

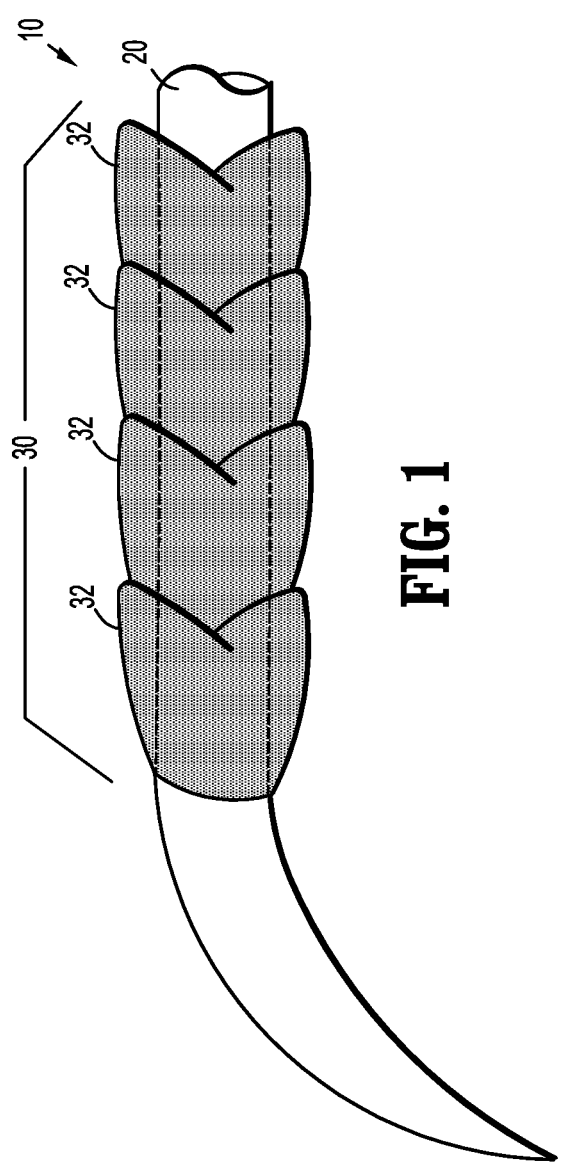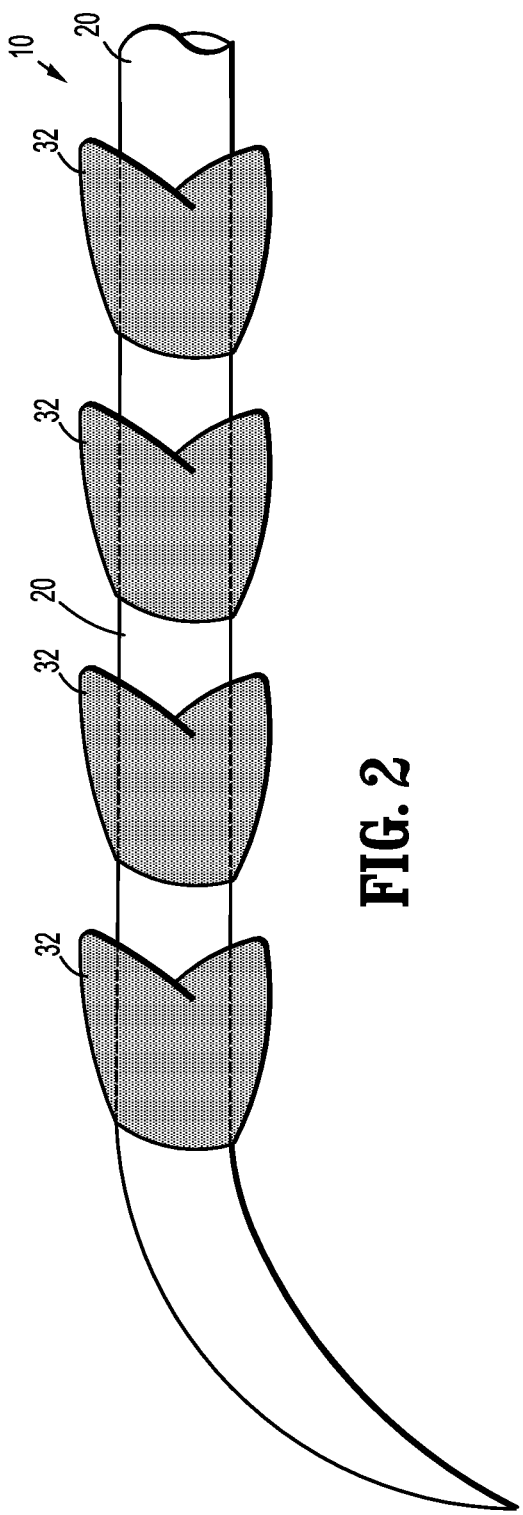
FIG. 1
FIG. 2

SUTURE WITH TENSION INDICATOR

CROSS-REFERENCE TO RELATED APPLICATION

This application claims the benefit of and priority to U.S. Provisional Patent Application No. 63/123,598 filed Dec. 10, 2020, the entire disclosure of which is incorporated by reference herein.

FIELD

This disclosure is directed to sutures for use in surgical procedures, which provide a visual indication when the suture is under excessive tension.

BACKGROUND

Anastomoses are often formed using sutures. In forming surgical anastomoses, the integrity and post-operative healing of the surgical anastomoses can be compromised by patient factors and surgical technique. Surgical technique is important in constructing a robust anastomosis, which means selecting a well-perfused section of tissue having sufficient mobilization of the tissues that are joined together, to prevent excessive tension at the anastomosis site.

An anastomosis under excessive tension has significantly greater chance of complications, such as leaks and bleeds. This is particularly seen in esophagectomies and colorectal surgeries, where end-to-end anastomosis (EEA) is performed. EEA includes joining 2 native tissues of the same organ, such as jejuno-jejunum, or it can be by joining different organs, such as esophagus and stomach. Adjoining different types of tissue impacts how the EEA heals, e.g., in esopha-gastric anastomosis, a 4 tissue-layered organ is joined with a 3-layered organ.

In cases where there is a high risk of anastomotic complications, the surgeon must have confidence in the robustness of the repair, especially for those cases where leaks have lethal outcomes, including low-anterior resections, rectal EEA, and/or esophagectomies. The amount of tension present at an anastomosis site is often determined by the individual surgeon, who decides based on experience if the tension is adequate for normal wound healing.

SUMMARY

One aspect of the disclosure is directed to sutures including an inner core having a first color and a Young's modulus from about 1 pound per square inch to about 5 pounds per square inch, and a segmented outer layer covering at least a portion of the inner core, the segmented outer layer having a second color which contrasts with the first color.

In aspects, the inner core has a Young's modulus from about 2 pounds per square inch to about 4 pounds per square inch.

In some aspects, the inner core has a % elongation from about 30% to about 80%. In other aspects the inner core has a % elongation from about 50% to about 75%.

In aspects, the first color of the inner core is provided by a fluorescent material. The fluorescent material may be selected from fluorescein, eosin, rhodamines, rhodols, bimanes, coumarins, umbelliferone, aminomethyl coumarins, dansyl, squarate dyes, benzofurans, fluorescent cyanines, rare earth chelates, carbazoles, derivatives thereof, or combinations thereof. The second color of the segmented outer layer may be provided by carbon black, bone black, D&C Green No. 6, or D&C Violet No. 2.

In aspects, a suture includes an inner core having a first color provided by a fluorescent material and a Young's modulus from about 1 pound per square inch to about 5 pounds per square inch, and a segmented outer layer covering at least a portion of the inner core, the segmented outer layer having a second color which contrasts with the first color.

In other aspects, a suture includes an inner core having a first color and a elongation from about 30% to about 80%, and a segmented outer layer covering at least a portion of the inner core, the segmented outer layer having a second color which contrasts with the first color.

Methods for repairing tissue with the sutures of the disclosure are also provided.

BRIEF DESCRIPTION OF THE DRAWINGS

Various aspects of the disclosed suture and methods are described herein below with reference to the drawings, wherein:

FIG. 1 is a side view of a suture prior to use;

FIG. 2 is a side view of the suture illustrated in FIG. 1 under tension;

DETAILED DESCRIPTION

Figure 3:
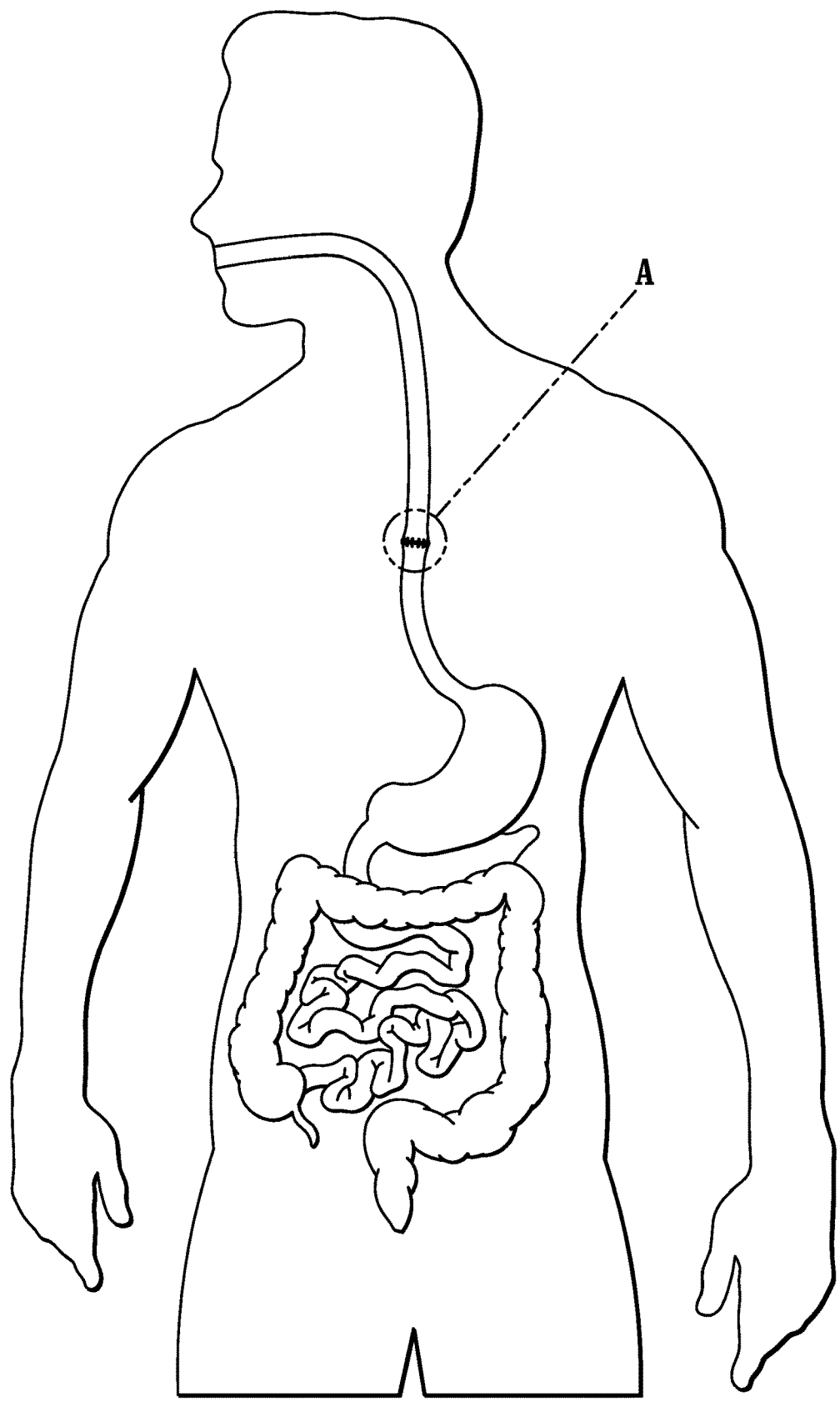
FIG. 3 is a view of an anastomosis within a patient.

The disclosed sutures and methods for their use will now be described in detail with reference to the drawings, in which like reference numerals designate identical or corresponding elements in each of the several views. However, it is to be understood that the disclosed aspects of the present disclosure are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure. In addition, directional terms such as front, rear, upper, lower, top, bottom, distal, proximal, and similar terms are used to assist in understanding the description and are not intended to limit the disclosure.

The disclosed sutures are multilayer, having an inner core at least partially covered by a segmented outer layer. Segments forming the segmented outer layer separate under tension, permitting visualization of the inner core of the suture. The inner core may be dyed with, or made of, colored materials, which enhance visualization of the core material of the suture in the surgical field, thereby alerting a surgeon or similar medical professional that the suture is under excessive, undesirable tension. This allows the surgeon to adjust the placement of the sutures during a surgical procedure and thus reduce the tension on the tissue at the suture line, which enhances healing of the sutured tissue.

Referring now in detail to the drawings, FIG. 1 shows a suture 10 having an inner core 20 surrounded by a segmented outer layer 30. Segmented outer layer 30 is formed of segments 32. The segments 32 of the segmented outer layer 30 are joined to inner core 20 to form suture 10. FIG. 1 shows the suture 10 in a relaxed state, where the suture 10 is not under excessive tension. As can be seen in FIG. 1, where the suture 10 is not under excessive tension, the segments 32 of the segmented outer layer 30 are in contact with each other, so that the inner core 20 of the suture 10 is not visible. In aspects, the segments 32 may assist in fastening the suture 10 to tissue.

However, if the suture 10 is subjected to excessive tension in use, as depicted in FIG. 2, the inner core 20 elongates so that the segments 32 of the segmented outer layer 30 are no longer in contact with each other, and the inner core 20 of the suture 10 becomes visible. As would be readily appreciated by the skilled artisan, as well as the surgeon or similar medical professional using the suture 10, the more tension that the suture 10 is subjected to will result in greater elongation and greater visibility of the inner core 20 of the suture 10.

Materials suitable for use in forming the inner core 20 and the segmented outer layer 30 of the suture 10 are within the purview of those skilled in the art. The inner core 20 and the segmented outer layer 30 of the suture 10 may be formed of bioabsorbable materials, non-bioabsorbable materials, or any combination thereof. The inner core 20 and the segmented outer layer 30 of the suture 10 may be formed of the same or different materials.

Suitable bioabsorbable materials used to form the inner core 20 and/or the segmented outer layer 30 of the suture 10 include, but are not limited to, absorbable polymers such as those formed of glycolide, glycolic acid, lactide, lactic acid, caprolactone, dioxanone, trimethylene carbonate, dimethyl trimethylene carbonate, copolymers (block or random) thereof, mixtures thereof, and/or blends thereof. Other suitable bioabsorbable materials used to form the inner core 20 and/or the segmented outer layer 30 of the suture 10 include, but are not limited to, collagen, chitin, chitin derivatives (e.g., chitosan), amino acid polymers (e.g., gelatin), polysaccharides (e.g., dextran), combinations thereof, and the like.

In aspects, the material used to form the inner core 20 of the suture 10 has a lower rate of bioabsorption than the material used to form the segmented outer layer 30 of the suture 10. A higher rate of bioabsorption of the segmented outer layer 30 may, in some applications, serve to enhance tissue ingrowth and subsequent healing and wound closure. In aspects, the inner core 20 of the suture 10 may be formed of bioabsorbable polymers, copolymers, or mixtures fabricated from polydioxanone, polycaprolactone, and polytrimethylene carbonate. The segmented outer layer 30 may be of bioabsorbable polymers, copolymers, or mixtures fabricated from glycolide or glycolic acid.

In other aspects, the suture 10 may be formed of non-absorbable, biocompatible materials. Such non-absorbable materials for forming the inner core 20 and/or the segmented outer layer 30 of the suture 10 include biocompatible polymeric materials which may be used in applications requiring a more permanent implantation of a prosthetic device. Such materials include polyesters (e.g., polyalkyl terephthalates), polyamides (e.g., nylon), polyurethanes, polycarbonates, polyimides, fluoropolymers, polyolefins, vinyl polymers, etc.

The materials used to form the inner core 20 of the suture 10 may have a Young's modulus from about 1 pound per square inch to about 5 pounds per square inch, in aspects from about 2 pounds per square inch to about 4 pounds per square inch, in other aspects from about 2.5 pounds per square inch to about 3.5 pounds per square inch, in yet other aspects about 3 pounds per square inch. The % elongation of the materials used to form the inner core 20 of the suture 10 may be determined using tests within the purview of the skilled artisan, including ASTM D-2256. The % elongation of the materials used to form the inner core 20 of the suture 10 may be from about 30% to about 80%, in aspects from about 50% to about 75%.

In aspects, the inner core 20 is a first color, and the segmented outer layer is a second color in contrast with the first color. The difference in color the inner core 20 and the segmented outer layer 30 of the suture 10 thus provides the suture 10 with a tension recognition feature, alerting the surgeon or similar medical professional that the suture 10 is under excessive, undesirable tension when the inner core 20 of the suture 10 is visible and that adjustments are necessary in the formation of an anastomosis with the suture 10.

In aspects, the first color imparted to the inner core 20 of the suture 10 may be a fluorescent material. Fluorescent materials include a wide range of pigments and dyes which "glow", sometimes referred to as "black light" and/or "black-light effects", when exposed to long-wave ultraviolet frequencies (UV). These UV frequencies are found in both sunlight and some artificial lights. Suitable dyes and/or pigments that can be used to color the inner core 20 of the suture 10 can be coated on the inner core 20 of the suture 10, or impregnated into the inner core 20 of the suture 10, e.g., by combining the fluorescent material with a polymer used to form the inner core 20 of the suture 10 during formation.

When a fluorescent material is exposed to light, the visible light component, sometimes to herein as "white light," tends to be reflected and perceived normally, as color. The UV component of the visible light is modified, sometimes referred to herein as "stepped down" energetically into longer wavelengths, producing additional visible light frequencies, which are then emitted alongside the reflected white light. The human eye perceives these changes into longer wavelengths as the glow associated with fluorescence.

There are both visible and invisible fluorescent materials. The visible fluorescent materials appear under white light to be a bright color, turning particularly brilliant under black lights. The invisible fluorescent materials appear transparent or pale under regular light, but will glow under UV light in a limited range of colors.

Suitable fluorescent materials include, but are not limited to, agents which are green or yellow fluorescent under visible light (e.g., fluorescein or eosin). Other suitable fluorescent materials include, but are not limited to, rhodamines, rhodols, and their derivatives; bimanes; coumarins and their derivatives such as umbelliferone and aminomethyl coumarins; aromatic amines such as dansyl; squarate dyes; benzofurans; fluorescent cyanines; rare earth chelates; carbazoles; derivatives thereof; and the like. Combinations of any of the foregoing may also be used.

As noted above, in aspects the segmented outer layer 30 is a second color different from the first color of the inner core 20 of the suture 10. Suitable dyes and/or pigments that can be used to color the segments 32 of the segmented outer layer 30 of the suture 10 can be coated on the segments 32 of the segmented outer layer 30, or impregnated into the segments 32 of the segmented outer layer 30, e.g., by combining the dyes and/or pigments with a polymer used to form the segments 32 of the segmented outer layer 30 of the suture 10 during formation. Suitable dyes include, but are not limited to, carbon black, bone black, D&C Green No. 6, and D&C Violet No. 2. A dye may be added to the segments 32 of the segmented outer layer 30 in a suitable amount, in aspects from about 0.05% by weight to about 1% by weight, in aspects about 0.1% by weight.

The suture 10 may be fabricated by any suitable polymer processing techniques. In aspects, the suture 10 may be formed by coextrusion, spinning, combinations thereof, and the like.

Exemplary extrusion devices and methods for forming sutures having a core and an outer layer include those disclosed, for example, in U.S. Pat. No. 5,626,611 and Vols. 4 and 6 of the Encyclopedia of Polymer Science and Engineering, (John Wiley & Sons, New York), c. 1986, pp. 812-832 and 571-631.

Exemplary spinning devices and methods for forming sutures having a core and an outer layer include those disclosed in in U.S. Pat. No. 5,626,611 and Volume 6 of the Encyclopedia of Polymer Science and Engineering, (John Wiley & Sons, New York), c. 1986, pp. 802-839.

Other polymer processing techniques used to form the disclosed sutures include, but are not limited to, casting, injection molding, and blow molding. In short, any polymer processing technique capable of forming the suture 10 having the inner core 20 and the segmented outer layer 30 adequately joined with the inner core 20 are contemplated to form the suture 10.

The segments 32 of the segmented outer layer 30 may be formed using any means within the purview of those skilled in the art. In aspects, the segments 32 of the segmented outer layer 30 are separately applied to the inner core 20 of the suture 10. In other aspects, an outer layer of material is applied to the inner core 20 of the suture 10, for example, by extrusion or coextrusion, and then the segmented outer layer 30 is cut at various locations in order to form the segments 32 on the segmented outer layer 30 of the suture 10.

The outer layer of material used to form the segmented outer layer 30 may be cut to form the segments 32 by any suitable means. In aspects (not shown), an apparatus used to make barbs on a suture may be adapted to cut the segmented outer layer 30 of the suture 10 to form the segments 32. The only requirement is any cutting of the segmented outer layer 30 should cut through the entirety of the material used to form the segmented outer layer 30 and but not cut the suture 10 in half.

Any suitable barb forming apparatus and method may be used to cut the segmented outer layer 30 of the suture 10, including the processes and apparatus disclosed in U.S. Pat. Nos. 9,687,227 and/or 10,728,429.

Figure 4:
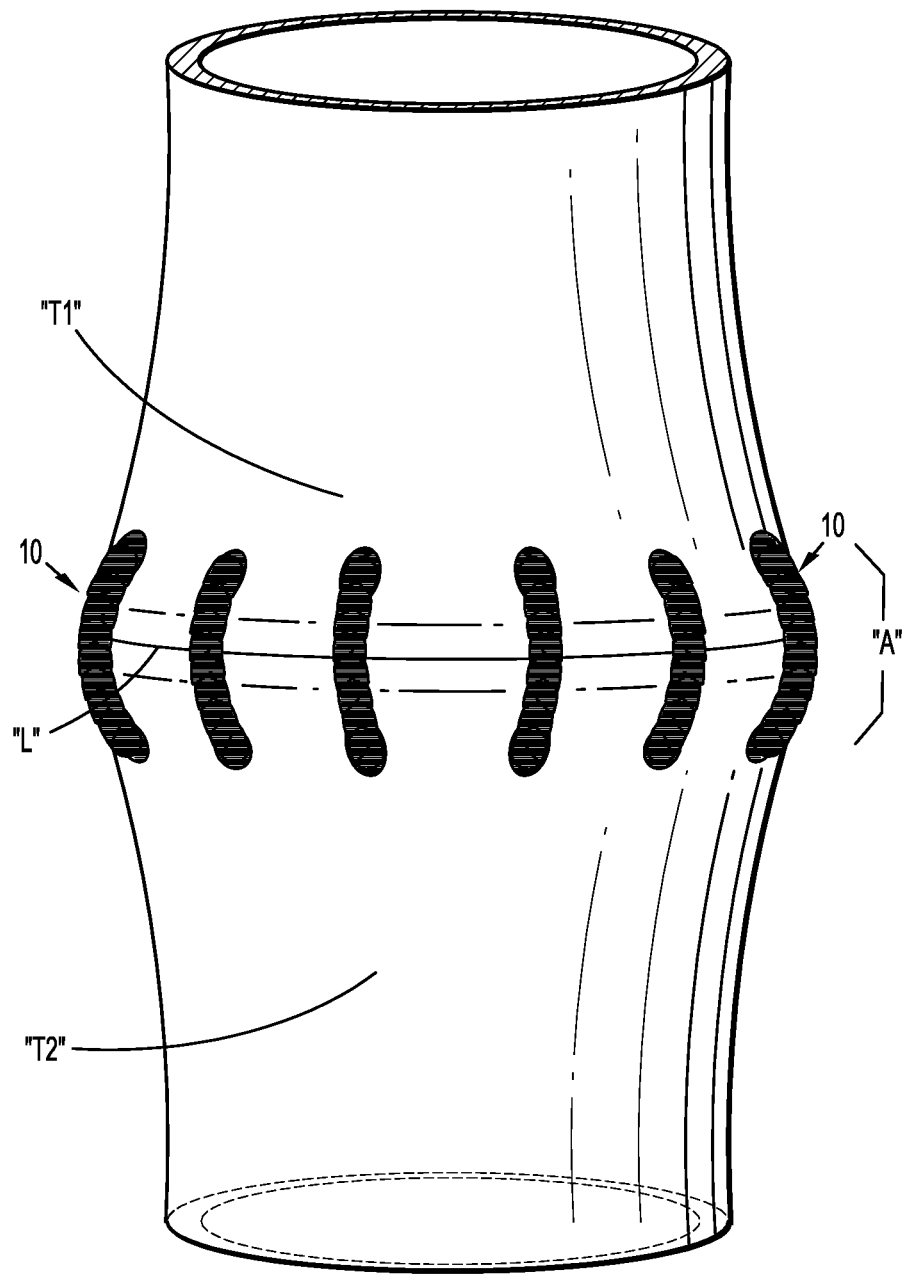
FIG. 4 is an enlarged view of the area of detail indicated by "A" in FIG. 3 that is not under tension.
Figure 5:
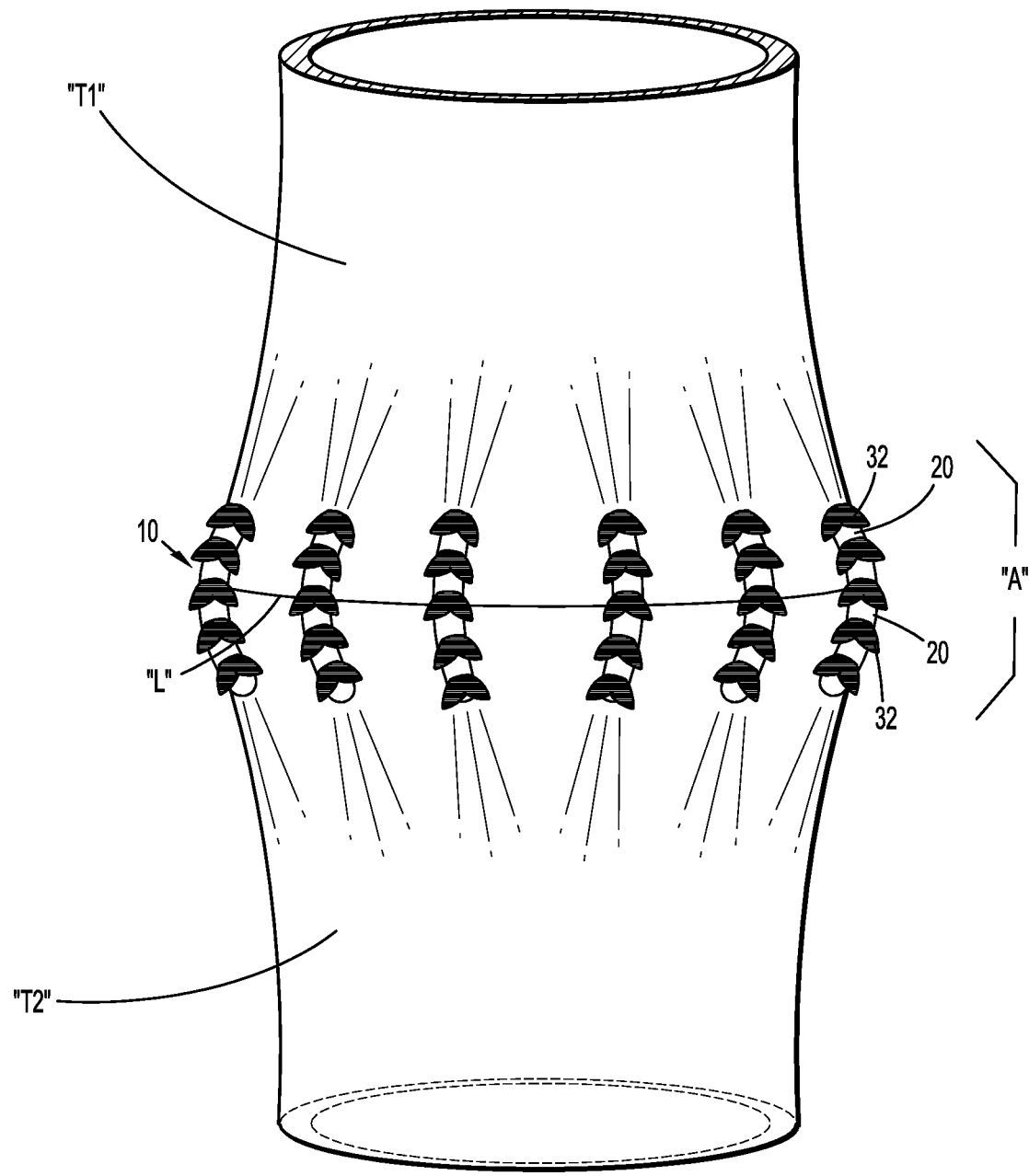
FIG. 5 is an enlarged view of the area of detail indicated by "A" in FIG. 3 that is under tension.

Use of the suture 10 to repair an anastomosis are set forth in FIGS. 3-5. FIG. 3 depicts use of the suture 10 in forming an esophageal anastomosis "A". As shown in FIG. 4, the sutures 10 used to form the esophageal anastomosis "A" join a tissue "T1" and a tissue "T2" at a suture line "L". The sutures 10 used to form the esophageal anastomosis are in a relaxed state, so the segments 32 of the segmented outer layer 30 are in contact with each other, and the inner core 20 of the suture 10 is not visible. This indicates the anastomosis is in a state of acceptable tension, and is the desired configuration for tissue repair.

If, however, as shown in FIG. 5, the sutures 10 used to form the esophageal anastomosis "A" are under tension, the inner core 20 extends so that the segments 32 of the segmented outer layer 30 are no longer in contact with each other, and the inner core 20 of the suture 10 is visible. The visibility of the inner core 20 of the suture 10 alerts the surgeon or similar medical professional that the suture 10 is under excessive, undesirable tension. This allows the surgeon to adjust the placement of the sutures 10 during the surgical procedure so that the anastomosis appears as depicted in FIG. 4. This results in a reduction of the tension on the tissue "T1" and "T2" at the suture line "L", which enhances healing of the sutured tissue.

In aspects, the suture 10 may be coated or impregnated with one or more materials which enhance its functionality, e.g., surgically useful substances, such as those which accelerate or beneficially modify the healing process when the material is implanted within a living organism. Thus, for example, antimicrobial agents such as broad spectrum antibiotics (gentamicin sulphate, erythromycin or derivatized glycopeptides) which are slowly released into the tissue can be incorporated to aid in combating clinical and sub-clinical infections in a surgical or trauma wound site.

Similarly, the suture 10 may be coated or impregnated with one or several substances to promote wound repair and/or tissue growth. Exemplary substances include polypeptides such as human growth factors. The term "human growth factor" or "HGF" embraces those materials, known in the literature, which are referred to as such and includes their biologically active, closely related derivatives. The HGFs can be derived from naturally occurring sources and are preferably produced by recombinant DNA techniques. Specifically, any of the HGFs which are mitogenically active and as such effective in stimulating, accelerating, potentiating or otherwise enhancing the wound healing process are useful herein. Growth factors contemplated for use in the materials of the present invention include hEGF (urogastrone), TGF-beta, IGF, PDGF, FGF, etc.

Advantages of the present disclosure include, but are not limited to:

Tension recognition feature for intraoperative assessment of tension at completed anastomosis or repair, with excessive tension indicated where inner core of suture is visible; and The suture can be used for any anastomosis, linear or circular, or in any applications where sutures are used to join layers of tissue, and/or to reinforce the tissue. It could apply to any soft tissue repair.

Persons skilled in the art will understand that the devices and methods specifically described herein and illustrated in the accompanying drawings are non-limiting exemplary aspects of the present disclosure. It is envisioned that the elements and features illustrated or described in connection with one exemplary aspect may be combined with the elements and features of another without departing from the scope of the disclosure. As well, one skilled in the art will appreciate further features and advantages of the disclosure based on the above-described aspects. Accordingly, the disclosure is not to be limited by what has been particularly shown and described, except as indicated by the appended claims.

What is claimed is:

1. A suture comprising:
   an inner core having a first color and a Young's modulus from about 1 pound per square inch to about 5 pounds per square inch; and
   a segmented outer layer fixed to and covering at least a portion of the inner core, the segmented outer layer having a second color which contrasts with the first color and segments which are in contact with each other when the suture is in a relaxed state, the segments separating from each other as a result of the suture being under tension.

2. The suture of claim 1, wherein the inner core has a Young's modulus from about 2 pounds per square inch to about 4 pounds per square inch.

3. The suture of claim 1, wherein the inner core has a % elongation from about 30% to about 80%.

4. The suture of claim 1, wherein the inner core has a % elongation from about 50% to about 75%.

5. The suture of claim 1, wherein the first color of the inner core is provided by a fluorescent material.

6. The suture of claim 5, wherein the fluorescent material is selected from fluorescein, eosin, rhodamines, rhodols, bimanes, coumarins, umbelliferone, aminomethyl coumarins, dansyl, squarate dyes, benzofurans, fluorescent cyanines, rare earth chelates, carbazoles, derivatives thereof, or combinations thereof.

7. The suture of claim 5, wherein the second color of the segmented outer layer is provided by carbon black, bone black, D&C Green No. 6, or D&C Violet No. 2.

8. A suture comprising:
an inner core having a first color provided by a fluorescent material and a Young's modulus from about 1 pound per square inch to about 5 pounds per square inch; and
a segmented outer layer fixed to and covering at least a portion of the inner core, the segmented outer layer having a second color which contrasts with the first color and segments which are in contact with each other when the suture is in a relaxed state, the segments separating from each other as a result of the suture being under tension.

9. The suture of claim 8, wherein the inner core has a Young's modulus from about 2 pounds per square inch to about 4 pounds per square inch.

10. The suture of claim 8, wherein the inner core has a % elongation from about 30% to about 80%.

11. The suture of claim 8, wherein the inner core has a % elongation from about 50% to about 75%.

12. The suture of claim 8, wherein the fluorescent material is selected from fluorescein, eosin, rhodamines, rhodols, bimanes, coumarins, umbelliferone, aminomethyl coumarins, dansyl, squarate dyes, benzofurans, fluorescent cyanines, rare earth chelates, carbazoles, derivatives thereof, or combinations thereof.

13. The suture of claim 8, wherein the second color of the segmented outer layer is provided by carbon black, bone black, D&C Green No. 6, or D&C Violet No. 2.

14. A suture comprising:
an inner core having a first color and a % elongation from about 30% to about 80%; and
a segmented outer layer fixed to and covering at least a portion of the inner core, the segmented outer layer having a second color which contrasts with the first color and segments which are in contact with each other when the suture is in a relaxed state, the segments separating from each other as a result of the suture being under tension.

15. The suture of claim 14, wherein the inner core has a % elongation from about 50% to about 75%.

16. The suture of claim 14, wherein the inner core has a Young's modulus from about 1 pound per square inch to about 5 pounds per square inch.

17. The suture of claim 14, wherein the inner core has a Young's modulus from about 2 pounds per square inch to about 4 pounds per square inch.

18. The suture of claim 14, wherein the first color of the inner core is provided by a fluorescent material.

19. The suture of claim 18, wherein the fluorescent material is selected from fluorescein, eosin, rhodamines, rhodols, bimanes, coumarins, umbelliferone, aminomethyl coumarins, dansyl, squarate dyes, benzofurans, fluorescent cyanines, rare earth chelates, carbazoles, derivatives thereof, or combinations thereof.

20. The suture of claim 18, wherein the second color of the segmented outer layer is provided by carbon black, bone black, D&C Green No. 6, or D&C Violet No. 2.

* * * * *